US005646028A

United States Patent [19]
Leigh

[11] Patent Number: 5,646,028
[45] Date of Patent: Jul. 8, 1997

[54] **ALKALINE SERINE PROTEASE *STREPTOMYCES GRISEUS* VAR. *ALKALIPHUS* HAVING ENHANCED STABILITY AGAINST UREA OR GUANIDINE**

[75] Inventor: Scott D. Leigh, Castro Valley, Calif.

[73] Assignee: The Clorox Company, Oakland, Calif.

[21] Appl. No.: 544,143

[22] Filed: Oct. 17, 1995

Related U.S. Application Data

[63] Continuation of Ser. No. 292,924, Aug. 18, 1994, abandoned, which is a continuation of Ser. No. 973,343, Nov. 6, 1992, abandoned, which is a continuation of Ser. No. 718,303, Jun. 18, 1991, abandoned.

[51] Int. Cl.$^6$ ............... C12N 9/52; C12N 9/50; C11D 7/42
[52] U.S. Cl. ............... 435/220; 510/392; 510/320; 435/219
[58] Field of Search ............... 435/212, 219, 435/220; 510/392, 320

[56] References Cited

U.S. PATENT DOCUMENTS

| | | | |
|---|---|---|---|
| 4,148,603 | 4/1979 | Schwager | 8/137 |
| 4,760,025 | 7/1988 | Estell et al. | 435/222 |
| 4,865,983 | 9/1989 | Durham | 435/264 |

FOREIGN PATENT DOCUMENTS

| | | |
|---|---|---|
| 50-35385 | 4/1975 | Japan . |
| 89/06279 | 7/1989 | WIPO . |
| 89/09819 | 10/1989 | WIPO . |

OTHER PUBLICATIONS

Awad et al (1972) *J. Biol. Chem* 247(13), 4144–4154.
Jurasek et al (1974) *Biochem, Biophys. Res. Comm.* 61(4) 1095–1100.
Gloptson et al (1975) *Biochemistry,* 14(6) 1168–1177.
Johnson et al (1974) *FEBS. Lett.* 47(1), 1–6.
Yoshida et al (1988) *J. Biochem.* 104, 451–456.
Suendsen et al (1991) FEBS Lett., 292(1,2) 165–167.
Henderson et al (1987) *J. Bacteriol.* 169(8) 3778–3784.
Delbger et al (1975) Nature, 257, 758–762.
Seber et al (1976) J. Biol. Chem., 251(1) 204–208.
Tsuyuki et al (1991) *J. Biochem.,* 110, 339–344.
Tsurushiin et al (1976) Sci. Rep. For Agr. Iburaki Univ 24, 107–118 in Biol Abstract (1978) 66(2), 1089, Abs. #11095.
Tsurushiin et al (1975) Sci. Rep Far Agr., Iburaki Univ. 23, 71–80 in Bio Abst. (1977) 63(8) 4608, Abs #46772.
Narahashi et al (1973) *J. Biochem.,* 73, 831–841.
Narahashi et al (1976) *J. Biochem.,* 79, 1119–1122.
Bauer et al (1973) Acta Chem. Scand., 27(9) 3147–3166 in Chem. Abst. (1974) 80(17), 135 Abstract #92547.
Wahlby (1969) *Biochem. Biophys, Acta,* 1985, 17885 in Chem Abst. (1969) 71 (19) 38, Abst #87876.
Jurasek et al,. "An Improved Fractionation System for Pronase on CM–Sephadex," *Canadian J. of Biochem.,* 49 (1971), pp. 1195–1201.
Henderson et al., "Characterization and Structure of Genes fdor Proeases A and B from *Streptomyces griseus,*" *J. Bacteriology,* 169:8 (1987), pp. 3778–3784.
Tsujibo et al., "Amino Acid Compositions and Partial Sequences of Two Types of Alkaline Serine Proteases for *Nocardiopsis dassonvillei* subsp. *prasina* OPC–210," *Agric Biol Chem,* 54(8) (1990), pp. 2177–2179.
Nakanishi et al., "Purification and Some Properties of an Alkalophilic Proteinase of a *Streptomyces Species,* " *Agr Biol Chem,* 38(1) (1974), pp. 37–44.
James et al., "Amino Acid Sequence Alignment of Bacterial and Mammalian Pancreatic Serine Proteases Based on Topological Equivalences," *Canadian J. Biochem,* 56 (1978), pp. 396–402.
Calbiochem Biochemical/Immunochemical Catalog 1990–1991: 193.
Narahashi et al., "Studies on Proteolytic Enzymes (Pronase) of *Streptomyces griseus* K–I, " *J. Biochem,* 73 (1973), pp. 831–841.
Narahashi et al., "Alkaline Proteinase E of *Streptomyces griseus* K–1," *J. Biochem,* 79 (1976), pp. 1119–1122.
Bauer et al., "Heterogeneity of *Streptomyces griseus* protease," *Acta Chem. Scand.,* 27(9) (1973), pp. 3147–3166, in *Chem. Abstract,* 80(17) (1974), p. 135, Abst. No. 92547.
Wahlby, "*Streptomyces griseus* protease," *Biochim. Biophys. Acta,* 185, (1969), pp. 178–185 in *Chem. Abstract,* 71(19) (1969), p. 38, Abst. No., 87876.
Church, et al., "Urea Denaturation of the Immobilized Proteases of *Streptomyces griseus* (pronase), " Dept. of Food Science and Biochemistry, North Carolina State University, Raleigh, NC, rev. Feb., 1992, pp. 1–2.

*Primary Examiner*—David M. Naff
*Assistant Examiner*—Jon P. Weber
*Attorney, Agent, or Firm*—Majestic, Parsons, Siebert & Hsue

[57] ABSTRACT

Purified native alkaline protease having an apparent molecular weight of 19,000 daltons and isolated from *Streptomyces griseus* var. *alkaliphilus* is provided, as well as methods of making and using the protease and cleaning compositions composed thereof.

11 Claims, 2 Drawing Sheets

```
SGPC  Y D L V G G D A Y Y I - G N G R C S I G F S V R
SGPA  - - I A G G E A I T T - G G S R C S L G F N V S
SGPB  - - I S G G D A I Y S - S T G R C S L G F N V R
ALP   A N I V G G I E Y S I N N A S L C S V G F S V T

SGPC  Q G S T P G F V T A G H C G S V G N A T T G F N
SGPA  V N G V A H A L T A G H C T N I S A S W S - - -
SGPB  S G S T Y Y F L T A G H C T D G A T T W W A N S
ALP   R G A T K G F V T A G H C G T V N A T A R I G -

SGPC  R V S Q - - G T F R G S W F P G R D M A W V A V
SGPA  - - - - - I G T R T G T S F P N N D Y G I I R H
SGPB  A R T T V L G T T S G S F P N N D Y G I V R Y
ALP   - - G A V V G T F A A R V F P G N D R A W V S L

SGPC  N S N W T P T S L V R D             V T G S
SGPA  S N P A A - A D G R V Y L Y N G S Y Q D I T T A
SGPB  T N T T I P K D G T V G - - - - - G Q D I T S A
ALP   T S A Q T - L L P P R V A N G S S F V T V R G S

SGPC  T Q A T V G S S I C R S G S T T G W R C G T I Q
SGPA  C N A F V G Q A V Q R S G S T T G L R S G S V T
SGPB  A N A T V G M A V T R G S T T G H S G S V T
ALP   T H A A V G - A V C R P G R T T G Y Q C G T I T

SGPC  Q H N T S V T Y - P Q G T I T G V T R T S A C A
SGPA  G L N A T V N Y G S S G I V I G M I O T N V C A
SGPB  A L N A T V N Y G G G D V V Y G M I R T N V C A
ALP   A K N V T A N Y - A E G A V R G L T Q G N A C M

SGPC  Q P G D S G G S - F I S G T Q A Q G V T S G G S
SGPA  Q P G D S G G S L F A G - S T A L G L T S G G S
SGPB  E P G D S G G F L Y S - G T R A L G L T S G G S
ALP   G R G D S G G S W I T S A G Q A Q G V M S G G N

SGPC  - - - - - G N C S I G - - - G T T F H Q P V N P
SGPA  - - - - - G N C R T G - - - G T T F Y Q P V T E
SGPB  - - - - - G N C S S G - - - G T T F F Q P V T E
ALP   V Q S N G N N C C I P A S Q R S S L F E R L Q P

SGPC  I L S Q Y G L T L V R S
SGPA  A L S A Y G A T V L - -
SGPB  A L S A Y G A S V Y - -
ALP   I L S Q Y G L S L V T G
```

ALKALINE SERINE PROTEASE *STREPTOMYCES GRISEUS* VAR. *ALKALIPHUS* HAVING ENHANCED STABILITY AGAINST UREA OR GUANIDINE

This is a continuation of application Ser. No. 08/292,924, filed Aug. 18, 1994, now abandoned; which was a contiuation of application Ser. No. 07/973,343, filed Nov. 6, 1992, now abandoned; which was a continuation of application Ser. No. 07/718,303, filed Jun. 18, 1991, now abandoned.

FIELD OF THE INVENTION

The invention pertains to the isolation and characterization of a *Streptomyces griseus* alkaline protease, to cleaning compositions containing the novel protease and to methods of cleaning using such compositions.

BACKGROUND OF THE INVENTION

A major trend in the detergent industry is to provide cleaning formulations that are functional at low wash temperature, are stable in the presence of laundry additives, and can be formulated as liquid, dry or granular compositions, while sufficient washing or cleaning ability is retained. These formulations generally require the use of enzymes, particularly proteases to fulfill this need.

In order to be useful as a detergent enzyme, it is desirable for a protease to possess proteolytic activity against proteinaceous substances over a wide pH and temperature range; exhibit catalytic stability in the presence of surfactants, builders, oxidizing agents and other detergent components; and maintain activity during storage (adequate shelf-life).

The most widely used proteases in cleaning compositions are the alkaline proteases derived from various strains of *Bacillus*. Such proteases, which are marketed by Novo/Nordisk Copenhagen, Denmark under trade names such as Esperase, Alcalase, or subtilisin Carlsberg, and Savinase, derived from *Bacillus licheniformis* have desirable alkaline stability properties and proteolytic activities. These enzymes have been well characterized and are widely used by detergent manufacturers. While effective in hot water washing, the temperature optima of the *Bacillus* enzymes is between 60°–70° C., which is above the normal temperatures used for warm (30°–40° C.) and cool (15°–30° C.) water washings. Moreover, the *Bacillus* alkaline proteases have less than desirable stability to oxidizing agents, and are completely unstable in chlorine bleaches, which precludes their use with chlorine bleaches, automatic dishwasher detergents, etc.

Variants of subtilisin, a serine protease produced by Gram-positive bacteria, have been produced using both random and site-directed mutagenesis of the subtilisin gene to affect changes in catalytic efficiency (value of $k_{cat}/K_M$), substrate specificity and tertiary structure. Specific subtilisin variants have also been characterized which show improved stability to oxidation, increased protease activity or improved washing ability (U.S. Pat. No. 4,760,025 issued Jul. 26, 1988 to Estell, et al; WO89/06279 published Jul. 13, 1989 to Hastrup, et al; and WO89/09819 published Oct. 19, 1989 to Bryan, et al).

*Streptomyces griseus*, an organism used for the commercial production of the alkaline protease "Pronase" (available from Calbiochem), secretes many extracellular proteins (Jurasek, et al (1971) *Can J Biochem* 49:1195–1201). Protease A and protease B, two of the serine proteases secreted by *S. griseus* strain IMRU 3499, have sequences which are 61% homologous on the basis of amino acid identity and 67% homologous in the coding region based on DNA identity (Henderson, et al (1987) *J Bacteriol* 169(8) :3778–3784). Japanese Patent No. 977824 titled "A Method of Manufacturing Alkaline Proteases" discloses the strain *S. griseus* var. *alkaliphilus* No. 33 (which is deposited with the Microbiology and Industrial Institute Microorganism Deposit No. 2086) and a method of obtaining a crude extract of an enzyme having an activity optimum at greater than pH 12 and proteolytic activity in 0.2 moles of sodium hydroxide solution.

Recently, a partial amino acid sequence of a third *S. griseus* protease, designated *S. griseus* alkaline protease (SGP), was reported in Tsujibo, et al (1990) *Agric Biol Chem* 54(8): 2177–2179. Based on a sequence comparison of the partial SGP sequence with the protease of the present invention, substantial amino acid differences are noted: $Arg_{15} \rightarrow Asp$; $Arg_{23} \rightarrow Ser$; and $Ser_{26} \rightarrow Ala$, all numbered in accordance with SEQ ID No. 1 herein. No further characterization of this enzyme has been reported.

Despite the existence of a multitude of known proteases and the application of recombinant DNA technology to the study and production of protease analogs, the art has yet to develop proteases completely satisfactory for use in modern cleaning formulations.

SUMMARY OF THE INVENTION

The present invention resides in the discovery of a novel alkaline protease which possesses improved proteolytic activity toward proteinaceous stains. This characteristic make the protease well suited for formulation into laundry detergents, automatic dishwasher detergents, pre-soaks, laundry additives, as well as other types of cleaning compositions.

The present provides an alkaline protease in substantially pure form comprising the N-terminal amino acid sequence (SEQ ID No: 1):

Tyr Asp Leu Val Gly Gly Asp Ala Tyr Tyr Ile Gly Asn Gly Arg Cys Ser Ile Gly Phe Ser Val Arg Gln Gly Ser Thr Pro Gly Phe Val Thr Ala Gly His Cys Gly Ser Val Gly Asn Ala Thr Thr Gly Phe Asn Arg Val Ser Gln Gly Thr Phe Arg Gly Ser Trp Phe Pro Gly Arg Asp Met Ala Trp Val Ala Val Asn Ser Asn Trp Thr Pro Thr Ser Leu Val Arg Asp;

and having an apparent molecular weight of about 19,000 daltons as determined by reducing SDS-polyacrylamide gel electrophoresis analysis.

This alkaline protease further comprising the C-terminal amino acid sequence (SEQ ID No:2):

Val Thr Gly Ser Thr Gln Ala Thr Val Gly Ser Ser Ile Cys Arg Ser Gly Ser Thr Thr Gly Trp Arg Cys Gly Thr Ile Gln Gln His Asn Thr Ser Val Thr Tyr Pro Gln Gly Thr Ile Thr Gly Val Thr Arg Thr Ser Ala Cys Ala Gln Pro Gly Asp Ser Gly Gly Ser Phe Ile Ser Gly Thr Gln Ala Gln Gly Val Thr Ser Gly Gly Ser Gly Asn Cys Ser Ile Gly Gly Thr Thr Phe His Gln Pro Val Asn Pro Ile Leu Ser Gln Tyr Gly Leu Thr Leu Val Arg Ser.

In one embodiment of the invention is provided a method of purifying the alkaline protease which method comprises:

(a) providing to a soluble extract having a pH of about 4 to about 6 and containing said protease, a chaotropic agent capable of dissociating said protease from a contaminating subtilisin-like protease in the soluble extract;

(b) applying the chaotrope-treated extract to an ion-exchange chromatography matrix to bind the dissociated protease;

(c) eluting the bound protease from the ion-exchange matrix;

(d) removing the chaotropic agent from the eluant; and (e) recovering a purified protease.

In yet another embodiment of the invention is provided a cleaning composition comprising a surfactant and in an amount effective to enhance removal of protein-containing materials, the alkaline protease described above.

In other embodiments the invention relates to a method of cleaning comprising contacting a surface soiled with proteinaceous material with an effective amount of the cleaning compositions provided above to enhance removal of protein-soiled materials.

BRIEF DESCRIPTION OF THE DRAWINGS

FIG. 1 is an alignment of the amino acid sequences of SGPC, SGPA, SGPB and alpha-lytic protease from *Lysobacter enzymogenes*. Dashed lines represent spaces inserted into sequences for alignment. Amino acids which are identical between SGPC and the other proteases are boxed.

DETAILED DESCRIPTION OF THE INVENTION

As used in this invention the term "*S. griseus* protease C" or "SGPC" refers to an alkaline protease having the primary sequence of the native, mature protein set forth in FIG. 1, top line. The term "alkaline" refers to a pH optimum of catalytic activity in the alkaline range, e.g., pH 7.0 to 11.0.

The primary sequence of SGPC provided in FIG. 1 is numbered in accordance to the number of residues present in the mature protein based on alignment with *S. griseus* protease A. However, for purposes of the present invention, reference may be made to the numbering of the primary sequence of the mature protein set forth in SEQ ID No. 1.

As used herein, an alkaline protease "derived from" a particular microorganism refers to the native enzyme isolated from *S. griseus* var. *alkaliphilus* No. 33. A deposit of this microorganism has been made at the American Type Collection, 12301 Parklawn Drive, Rockville, Md. under the accession number ATCC 55178. The derived enzyme is not necessarily physically derived from the microorganism but may be generated in any manner including, for example, expression from a recombinant microbial host.

Although there may be slight variations in the sequence of a naturally occurring enzyme within a given species of organism, enzymes of a specific type produced by organisms of the same species generally are substantially identical with respect to substrate specificity, thermal stability, activity levels under various conditions (e.g., temperature and pH), oxidative stability, and the like. Thus for purposes of the present invention, it is contemplated that other strains of *S. griseus* may also produce SGPC and thus may be used as a source of SGPC.

General Method

The practice of the present invention will employ, unless otherwise indicated, conventional techniques of protein purification, molecular biology, microbiology, recombinant DNA techniques and protein sequencing, which are within the skill of the art. Such techniques are explained fully in the literature. See, e.g., *A Practical Guide to protein and Purification for Microsequencing*, (P. T. Matsudaira, ed., (1989) Academic Press, Inc.); Sambrook, Fritsch & Maniatis, *Molecular Cloning; A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); *PCR Protocols, A Guide to Methods and Applications* (M. A. Innis, et al, eds., (1990) Academic Press, Inc.); *Current Protocols in Molecular Biology* (F. M. Ausubel, et al, eds., (1989) John Wiley & Sons); *Laboratory Techniques in Biochemistry and Molecular Biology*, Vol. 9, G. Allen, SeCond Edition (1989) Elsevier; and additional publications in the series, *Methods in Enzymology* (Academic Press, Inc.). All patents, patent applications, and publications mentioned herein, both supra and infra, are hereby incorporated by reference.

Enzyme Preparation

To isolate the alkaline protease of the present invention, the microorganism is grown in a suitable growth medium until the culture registers its highest level of secreted proteolytic activity. The composition of the growth medium will depend upon the particular microorganism involved. Growth media will typically contain assimilable sources of carbon and nitrogen, energy sources, magnesium, potassium and sodium ions, and optionally amino acids and purine and pyrimidine bases.

*S. griseus* generally secretes many of the native enzymes it produces directly into the media. The microbial cells are generally removed from the media components by centrifugation, and the resulting supernatant, which contains a crude extract of the desired protease, is dialyzed. Optionally, the supernatant may be concentrated and clarified by filtration or other conventional methods prior to subsequent purification procedures.

If a commercial alkaline protease preparation such as "alkaline protease" from *S. griseus* (available from Calbiochem) is used as the initial source of SGPC, one may eliminate the above procedure and begin directly with the dialysis step. The purification of SGPC from fermentation components or other proteases in alkaline protease from *S. griseus*, both of which include a contaminating subtilisin-like protease of approximately 27,000 daltons, is best performed in a chaotropic environment. A chaotropic agent (i.e., a mild protein denaturant that dissociates hydrogen bonds and affects the tertiary structure of proteins) is used. Examples of chaotropes include urea and guanidine hydrochloride, with urea being preferred.

The concentration of the chaotropic agent in the crude extract will depend upon the particular agent that is used. In the case of urea, concentrations (final) between about 4 M and 8 M, preferably about 6 M, will be used in batch processes at 4° C. The concentrations for guanidine hydrochloride will typically be about 2 M to about 4 M. Temperatures in the range of 4° C. to 10° C. will normally be used, with 4° C. being used for convenience. Mixing will typically be used to enhance contact between the chaotropic agent and the crude extract containing the SGPC enzyme that is in association with other contaminating proteins.

After the chaotropic agent is added to the supernatant, the resulting aqueous solution is applied to an ion-exchange chromatography matrix, such as Mono-S Sepharose or S Sepharose, to separate SGPC from any contaminating bacterial proteases on the basis of differences in their isoelectric points. In a pH 5.0 buffer, SGPC binds to the cation exchange matrix, whereas the 27,000 dalton contaminating protease does not. Elution of SGPC may be preformed using a linear salt gradient, for example, 30 mM to 125 mM of NaCl.

The eluant is then dialyzed to remove the chaotropic agent. Dialysis may be performed in 5–20 mM $NH_4OAc$, pH 5.0 at 4° C.

If the protease is being isolated from a microorganism culture, it may be necessary to add a further ion-exchange chromatography step to remove such media contaminants such as casein. Cationic exchange matrices such as the ones mentioned above, performed in the absence of urea, are suitable for this purpose.

SDS-polyacrylamide gel electrophoresis (PAGE) may be used to analyze the protease which appears as a single band having an apparent molecular weight of 19,000 under reducing conditions.

Once substantially purified, the native SGPC may be subjected to amino acid sequence analysis. Applying conventional peptide sequencing procedures, using for example, an Applied Biosystems model A70A gas-phase sequencer or a MilliGen ProSequencer™ 6600 solid-phase sequencer, amino acid sequences of SGPC may be generated.

Given the amino acid sequence determination of SGPC, recombinant polypeptides encoding the protease may be prepared. First, oligonucleotide probes encoding a portion of the determined amino acid sequence are prepared and used to screen DNA libraries for the gens encoding SGPC. The basic strategies for preparing oligonucleotide probes and DNA libraries, as well as their screening by nucleic acid hybridization, are well known to those of ordinary skill in the art. See, for example, *DNA Cloning: Volume I* (D. M. Glover, ed. 1985); *Nucleic Acid Hybridization*, supra; *Current Protocols in Molecular Biology*, supra; and *Molecular Cloning: A Laboratory Manual*, supra.

First, a DNA library is prepared. The library can consist of a genomic DNA library from *S. griseus*. DNA libraries can also be constructed of cDNA prepared from a poly-A RNA (mRNA) fraction by reverse transcription. The mRNA is isolated from a cell line known to express the protease. The cDNA (or genomic DNA) is cloned into a vector suitable for construction of a library. A preferred vector is a bacteriophage vector, such as phage lambda. The construction of an appropriate library is within the skill of the art.

Once the library is obtained, oligonucleotides to probe the library are prepared and used to isolate the desired SGPC gens. The particular nucleotide sequences selected are chosen so as to correspond to the codons encoding a known amino acid sequence from SGPC. Since the genetic code is redundant, it will often be necessary to synthesize several oligonucleotides to cover all, or a reasonable number, of the possible nucleotide sequences which encode a particular region of the protein. One can also design a single probe or "guessmer" wherein one uses codon bias and other considerations, such as CG dinucleotide underrepresentations to guess the best sequence, or by using inosine bases where ambiguity in the sequence exists (Sambrook, et al, supra). It may also be desirable to use two probes (or sets of probes), each to different regions of the gene, in a single hybridization experiment. Automated oligonucleotide synthesis has made the preparation of probes relatively straightforward. In addition, probes may be commercially obtained.

Alternatively, one may use the polymerase chain reaction (PCR) to amplify a portion of the desired gene encoding the protease. In its simplest form, PCR is an in vitro method for the enzymatic synthesis of specific DNA sequences, using two oligonucleotide primers that hybridize to opposite strands and flank the region of interest in the target DNA. A repetitive series of cycles involving template denaturation, primer annealing, and the extension of the annealed primers by DNA polymerase results in the exponential accumulation of a specific fragment whose termini are defined by the 5' ends of the primers. PCR reportedly is capable of producing a selective enrichment of a specific DNA sequence by a factor of $10^9$. The PCR method is described in Saiki, et al (1985) *Science* 230:1350 and is the subject of U.S. Pat. Nos. 4,683,195; 4,683,202 and 4,800,159. The portion of the SGPC gene synthesized by the PCR technique will be used to probe cDNA libraries for clones encoding the full length SGPC cDNA.

Because the genetic code is redundant, PCR from known amino acid sequence requires PCR with either degenerate, inosine substituted, or "guessmer" PCR oligos. (See PCR Protocols, Innis, et al, supra, especially the chapter on "Degenerate Primers for DNA Amplification" at pp. 39–45; Sambrook, et al, supra; Maisonpiere, et al (1990), *Science* 247:1446; Hohn, et al (1990) *Nature* 344:339). These techniques have been widely used to clone a variety of genes as described in the above references. One can use PCR to amplify DNA sequences from either cDNA generated from RNA, genomic DNA or from a cDNA or genomic library. Strategies using either conventional PCR as described above, or "anchor" PCR could be used. In anchor PCR, one uses a library containing the SGPC gene as the PCR template, and uses one sequence within the SGPC gene and another within the vector that the library is in so that the region amplified contains sequences from the vector as well as from the SGPC gene. In this case only very limited amino acid information is necessary. PCR conditions and components such as temperatures, concentrations of magnesium, Taq polymerase, and oligos would be optimized as described in Innis, et al, supra. one might also utilize conditions where 7-deazaguanine is used to allow the amplification of sequences containing secondary structure.

As an alternative to cloning the gene based on nucleic acid probes, one can use the amino acid sequence of SGPC to prepare antibody probes that can be used to screen for the SGPC gene. Given the amino acid sequence, peptides of identical sequence can be synthesized by standard techniques, and these peptides can be used to immunize rabbits or mice. Polyclonal or monoclonal antibodies to either SGPC or peptides derived therefrom can be generated and used to detect SGPC clones from an appropriate library. Libraries made in vectors which are designed to express the gene of interest, include but not limited to lambda gt11, lambdaZAP, or lambdaORF8 (see Ausubel, et al, supra, and Sambrook, et al, supra) can be screened with an antibody to that library. Libraries in these vectors can be generated or purchased from sources such as Clontech or Stratagene. The protein of the cloned gene is expressed in these vectors and the ability of an antibody to bind to the expressed protein allows one to identify the SGPC clone by standard antibody probing techniques.

A DNA molecule containing the coding sequence for the SGPC protease can be cloned in any suitable expression vector and thereby maintained in a composition substantially free of vectors that do not contain the coding sequence of other Streptomycete-derived genes, including those encoding other protease activities. Numerous expression vectors are known to those of skill in the art, and the selection of an appropriate expression vector is a matter of choice.

Cleaning Compositions

The protease of this invention may be combined with detergents, builders, bleaching agents and other conventional ingredients to produce a variety of novel cleaning compositions useful in the laundry and other cleaning arts such as, for example, laundry detergents (both powdered and liquid), laundry pre-soaks, all fabric bleaches, automatic dishwashing detergents (both liquid and powdered), and household cleaners, particularly drain openers. In addition, the protease may also be employed in the cleaning of contact lenses and other membranes by contacting such materials with an aqueous solution of the cleaning composition.

The protease-containing cleaning compositions of the invention include laundry detergents, laundry pre-soaks, (bleaches) and automatic dishwashing detergents. The composition of such products is not critical to this invention, and the same may be readily prepared by combining an effective amount of the SGPC enzyme preparation with the conventional components of such compositions in their art recognized amounts.

Surfactants

The cleaning compositions of the present invention include at least one surfactant selected from the anionic, cationic and nonionic surfactants. Particularly effective surfactants appear to be nonionic surfactants. Preferred surfactants of use include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides, and their ethoxylated derivatives.

Anionic surfactants may also be suitable. Examples of such anionic surfactants may include the ammonium, substituted ammonium (e.g., mono-, di-, and triethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, olefin sulfonates, hydroxyalkane sulfonates, fatty acid monoglyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Further, suitable amphoteric and zwitterionic surfactants which contain an anionic water-solubilizing group, a cationic group and a hydrophobic organic group may include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds. Other examples of potentially suitable zwitterionic surfactants can be found described in U.S. Pat. No. 4,005,029, at columns 11–15, which are incorporated herein by reference.

Further examples of anionic, nonionic, cationic and amphoteric surfactants which may be suitable for use in this invention are depicted in Kirk-Othmer, *Encyclopedia of Chemical Technology*, Third Edition, Volume 22, pages 347–387, and *McCutcheon's Detergents and Emulsifiers*, North American Edition, 1983, which are incorporated herein by reference.

Detergent Builders

Detergent compositions of the present invention can optionally comprise inorganic or organic detergent builders to assist in mineral hardness control. These builders can comprise from 0 to about 80% by weight of the composition. When included, these builders typically comprise up to about 60% by weight of the detergent composition. Built liquid formulations preferably comprise from about 10 to about 25% detergent builder while built granular formulations preferably comprise from about 10 to about 50% by weight detergent builder.

Suitable detergent builders include the crystalline aluminosilicate ion exchange materials disclosed in U.S. Pat. No. 4,661,288 which is incorporated herein by reference.

Other examples of detergent builders include the various water-soluble, alkali metal, ammonium or substituted ammonium phosphates, polyphosphates, phosphonates, polyphosphonates, carbonates, silicates, borates, polyhydroxysulfonates, polyacetates, carboxylates, and polycarboxylates. Preferred are the alkali metal, especially sodium, salts of the above.

Other Optional Detergent Ingredients

Other optional ingredients which can be included in detergent compositions of the present invention, in their conventional art-established levels for use (i.e., from 0 to about 20%), include solvents, bleaching agents, bleach activators, soil-suspending agents, corrosion inhibitors, dyes, fillers, germicides, pH adjusting agents (monoethanolamine, sodium carbonate, sodium hydroxide, etc.), enzyme stabilizing agents, perfumes, fabric softening components, static control agents, and the like.

Dyes include anthraquinone and similar blue dyes. Pigments, such as ultramarine blue (UMB), may also be used, and can have a bluing effect by depositing on fabrics washed with a detergent bleach containing UMB. Monastral colorants are also possible for inclusion.

Optical brighteners such as stilbene, styrene and styrl-naphthalene brighteners (fluorescent whitening agents), may be included. Fragrances used for esthetic purposes are commercially available from Norda, International Flavors and Fragrances and Givaudon. Stabilizers include hydrated salts, such as magnesium sulfate, and boric acid.

Detergent Formulations

Granular or dry formulations embodying the detergent compositions of the present invention can be formed by conventional techniques, i.e., by slurrying the individual components in water and then atomizing and spray-drying the resultant mixture, or by pan or drum granulation of the ingredients. Granular formulations preferably comprise from about 10 to about 30% detergent surfactant, usually anionic. Dry formulations will generally comprise from about 0.5–2.5% by weight of the protease enzyme preparation.

Liquid formulations embodying the detergent compositions can be built or unbuilt. If unbuilt, these compositions conventionally contain approximately 15 to 50% total surfactant, from 0 to 10% of an organic base such as a mono-, di-, or tri-alkanol amine, a neutralization system such as an alkali metal hydroxide and a lower primary alcohol such as ethanol or isopropanol, and approximately 20 to 80% water. Such compositions are normally homogeneous single phase liquids of low viscosity (approximately 100 to 150 centipoise at 75° F.). Preferably, liquid detergent compositions of the present invention contain from about 0.5–2.5% by weight of the protease enzyme preparation.

Built liquid detergent compositions can be in the form of single phase liquids provided that the builder is solubilized in the mixture at its level of use. Such liquids conventionally contain 10 to 25% total surfactant, 10 to 25% builder which can be organic or inorganic, 3 to 10% of a hydrotrope system and 40 to 77% water. Liquids of this type also have a low viscosity (100 to 150 centipoise at 75° F.). Built liquid detergents incorporating components that form heterogeneous mixtures (or levels of builder that cannot be completely dissolved) can also comprise detergent compositions of the present invention. Such liquids conventionally employ viscosity modifiers to produce systems having plastic shear characteristics to maintain stable dispersions and to prevent phase separation or solid settlement.

The following examples serve to give specific illustration of the practice of this invention, but they are not intended in any way to act to limit the scope of the appended claims.

EXAMPLES

Growth of *Streptomyces griseus* var. *alkaliphilus* No. 33

A lyophile of the *Streptomyces griseus* var. *alkaliphilus* No. 33 was obtained from the Microbiology and Industrial Institute in Japan (deposit number 2086). The lyophile was reconstituted and propagated in a medium containing 2% soluble potato starch, 1% casein, 0.5% corn steep liquor, 0.3% $K_2HPO_4$, .005% $MgSO_4 \cdot 7H_2O$, and 2% $Na_2CO_3$. Growth was at 30° C. for 12 days until the culture registers its highest level of secreted proteolytic activity.

Assay for Proteolytic Activity

Protease activity was assayed with the use of the synthetic substrate, succinyl-Ala-Ala-Pro-Phe-para-nitroanilide (sAAPFpNA) (SEQ ID NO. 3). The activity was monitored by the release of para-nitroaniline at 405 nm using a microtiter plate reader. The assay mixture was composed of 10 ul of enzyme solution diluted with 50 ul of 100 mM sodium bicine, pH 8.0, 30 ul $H_2O$ and 10 ul of 20 mM sAAPFpNA. Assays were performed at room temperature.

Purification of SGPC from *S. griseus* var. *alkaliphilus*

One liter cultures were subjected to centrifugation (7,000 x g, 4° C., 10 min) to remove cells. The supernatant was then filtered through 0.45 um filters to remove particulates and partially clarify the solution. The supernatant was then dialysed against 20 mM $NH_4OAc$, pH 5.0 at 4° C. to remove salts and lower the pH prior to chromatography. Immediately before chromatography, an aliquot of the dialysed supernatant was brought to 6 M urea by adding solid urea directly to the supernatant. The supernatant was filtered once more through 0.45 um filters then loaded onto a HiLoad S Sepharose FF 26/10 column equilibrated in 20 mM NH40Ac pH 5.0, 6 M urea (buffer A) at 4° C. After washing the column with buffer A, a step gradient was formed by washing the column with buffer A containing 30 mM, 75 mM, 100 mM, 125 mM, 200 mM, and 1000 mM NaCl. The protease of interest was eluted between 75 mM and 100 mM NaCl. Fractions containing activity were pooled, dialysed into 5 mM $NH_4OAc$, pH 5.0, then lyophilized.

An aliquot of the dialysed pool was subjected to polyacrylamide gel-electrophoresis (PAGE) in the presence of sodium dodecyl sulphate (SDS) according to Laemmli, (1970) *Nature* 227:680–685. Samples were prepared by first inactivating the protease with 1 mM PMSF at room temperature for 15 min, then boiling for 3 min in the presence of SDS. Ultrathin homogeneous 20% acrylamide gels were run using the PhastSystem (Pharmacia) and stained with silver. The gels indicated that a single band with a reduced molecular weight of approximately 19,000 was present with a smear of material running at the dye front. This material at the dye front presumably represents media components which copurify with the protease and could successfully be separated from the protease by loading the material onto a second cation-exchange column run this time in the absence of urea.

The lyophilized material was resuspended into 20 mM $NH_4OAc$, pH 5.0 (buffer B), filtered, then loaded onto a Mono S 5/5 column equilibrated in buffer B. Washing the column with buffer B removed the contaminating media components and the protease was then eluted with buffer B containing 75 mM NaCl. Analysis of this material by SDS-PAGE indicated a single band at approximately 19,000 daltons.

Wash Performance Test

The wash performance of the SGPC (purified as described above) was compared to that of the commercially utilized detergent protease Savinase in beaker-scale studies. Grass stain removal from cotton swatches, at 37° C., in a solution prepared using powdered detergent (104 g/69 liters) at pH 10.5, was measured on an equal weight basis (0.25 mg protease/500 ml wash liquor). Results are expressed as percent stain removal over a control containing no enzyme and are summarized below.

TABLE

| Enzyme | (delta) % SRE |
|---|---|
| Savinase | 49.8 |
| SGPC | 59.6 |

These results show that SGPC was more effective than Savinase against grass stain used at equal weight of protease in the wash liquor.

Sequence of SGPC

The SGPC purified from the alkaline protease from *S. griseus* (Calbiochem) was subjected to reverse-phase high performance liquid chromatography (HPLC) on a $C_4$ column in 0.1% trifluoroacetic acid (TFA) with a 40 min gradient at 0.8 ml/min from 0 to 90% acetonitrile in 0.1% TFA. The SGPC eluted as a single peak with a retention time of approximately 26 min. This additional chromatographic step served to further purify the protein and irreversibly inactivate the protein. The inactivated protein was brought to dryness using vacuum centrifugation and then used as the substrate for enzymatic digestions or chemical cleavages.

Sequencing grade trypsin, endoproteinase Asp-N, asparaginylendoproteinase (Asn-C), and endoproteinase Lys-C were employed to generate internal fragments of the protease. For the tryptic digestions, the inactivated protein was first carboxymethylated at cystsine residues (*A practical Guide to Protein and Peptide Purification for Microsequencing*, supra), then digested with trypsin (from Promega) as directed by the manufacturer. For the Asp-N and Asn-C digestions, the inactivated protein was first digested with the Asp-N (from Boehringer) and Asn-C (from Takara) as directed by the manufacturer, then carboxymethylated as above. For the Lys-C digestions, the inactivated protein was first S-aminoethylated at cystsine residues using the following procedure. The inactivated SGPC was dissolved in 50 ul of 8 M urea\0.4 M $NH_4HCO_3$ pH 7.8 then treated with 5 ul of 45 mM dithiothreitol for 15 min at 50° C. At this point, 5 ul of 100 mM N-(iodoethyl)-trifluoroacetamide (Aminoethyl-8™ from Pierce) in methanol was added and the incubation was continued at 50° C. for one hour. An additional 5 ul of the Aminoethyl-8™ was added, and the incubation continued at 50° C. for two more hours. After cooling to room temperature, the modified SGPC was then digested with Lys-C (from Promega) as directed by the manufacturer.

Chemical cleavage was performed using cyanogen bromide (CNBr from Kodak) as directed in *A Practical Guide to Protein and Peptide Purification for Microsequencing*, supra. The protein was then carboxymethylated as before.

The fragments produced by the enzymatic digestions were separated by reverse-phase HPLC on a $C_{18}$ column in 0.1% TFA with a 59 min gradient at 0.8 ml/min from 57% to 90% acetonitrile in 0.1% TFA. The fragments produced by the CNBr cleavages were separated by reverse-phase HPLC on a $C_4$ column in 0.1% TFA with a 40 min gradient at 0.8 ml/min from 0 to 90% acetonitrile in 0.1% TFA. The purified peptides were brought to dryness by vacuum centrifugation and then coupled to derivatized membrane disks (MilliGen/Biosearch) as directed by the manufacturer.

The covalently coupled peptides were subjected to automated Edman degradation using a MilliGen ProSequencer™ 6600 solid-phase sequencer using the manufacturers' chemicals and protocols.

Sequencing of the SGPC isolated from *Streptomyces griseus* var. *alkaliphilus* No. 33 by the above methods indicated that both sources of SGPC yield enzymes with identical sequences. Sequencing by the methods detailed above provided overlapping fragments which enabled the construction of the amino acid sequence except for one missing fragment which occurs after residue $Asp_{81}$. As can be seen in FIG. 1, this gap occurs in a region in which there is no sequence identity among the other proteases and given the size of the region in the other proteases, the gap in SGPC is likely to be between three and eight amino acids in length.

Inhibition of SGPC

The effects of various protease inhibitors were tested by preincubating the inhibitor with SGPC for a prescribed amount of time, then determining the residual activity. The SGPC at 50 ug/ml in 100 mM sodium bicine, pH 8.0, was incubated at 25° C. for 10 min and 30 min with the indicated concentrations of the following inhibitors: phenylmethylsulfonyl fluoride (PMSF), diisopropyl fluorophosphate (DFP), ethylenediaminetetraacetic acid (EDTA), and iodoacetic acid (IOAc). Following the incubation period, the enzyme was immediately assayed by combining 5 ul of the inhibited enzyme with 50 ul of sodium bicine, pH 8.0, 35 ul of water, and 10 ul of 20 mM succinyl-Ala-Ala-Pro-Phe-para-nitroanilide (sAAPFpNA) (SEQ ID NO. 3) in a well of a microtiter plate. Rates were determined at 25° C. using a microtiter plate reader. Results were reported as % remaining activity compared to a noninhibited control.

| Inhibitor | 10 min | 30 min |
| --- | --- | --- |
| No Inhibitor | 100% | 100% |
| 1.0 mM PMSF | 0.07% | 0.06% |
| 1.0 mM DFP | 23.7% | 1.7% |
| 5.0 mM DFP | 0.5% | 0.08% |
| 5.0 mM EDTA | 97% | 94% |
| 5.0 mM IOAc | 104% | 103% |

These results show that both PMSF and DFP inhibit SGPC, which would be expected for a serine protease. There was no significant inhibition by EDTA, which inhibits most metallo-proteases, or IOAc, which inhibits most cysteine proteases. The results indicate that PMSF is a better inhibitor for this enzyme, since at 1.0 mM PMSF, virtually all of the SGPC is inhibited in the first 10 min of incubation. In contrast, higher concentrations of DFP and longer incubation times are required to achieve the same level of inhibition. The difference in the effectiveness of these two inhibitors could be explained by the molecular size of the two inhibitors and how it would be accommodated in the binding pocket of the enzyme. PMSF, being larger and containing an aromatic ring, presumably is better positioned in the binding pocket as opposed to DFP, which is smaller and contains no aromatic ring. The preference for PMSF suggests that the enzyme would be more active in cleaving proteins on the C-terminal side of hydrophobic residues, such as phenylalanine, than smaller amino acids like alanine or valine.

Substrate Specificity of SGPC

The enzyme was assayed with a series of tetrapeptide substrates which had the form succinyl-Ala-Ala-Pro-X-para-nitroanilide (sAAPXpNA) (SEQ ID NOS. 3–20), where X is the P1 amino acid (the residue found on the N-terminal side of the bond which is cleaved). Kinetics constants $k_{cat}$ and $K_m$ were determined by assaying an appropriate dilution of SGPC with eight different concentrations of each substrate. Each substrate was dissolved in 100% DMSO to a concentration of 100 mM with the exception of sAAPQpNA (SEQ ID NO. 13) which was soluble only to a concentration of 15 mM. Five ul of an appropriate dilution of SGPC was placed in the wells of a microtiter dish. The reaction was initiated by adding 95 ul of the reaction mixture which was comprised of 50 ul of sodium bicine, pH 8.0, 35 ul of water, and 10 ul of the appropriate concentration of substrate in DMSO. The final concentration of DMSO was 10% in all of the reactions. All substrate concentrations were done in triplicate and rates were determined at 24° C. using a microtiter plate reader. The results are presented below.

| Substrate | $k_{cat}$ (S$^{-1}$) | $K_m$ (mM) | $k_{cat}/K_m$ (M$^{-1}$ S$^{-1}$) |
| --- | --- | --- | --- |
| sAAPFpNA (SEQ ID No. 3) | 39.7 | 0.29 | 137,600 |
| sAAPMpNA (SEQ ID No. 4) | 39.3 | 0.39 | 100,400 |
| sAAPYpNA (SEQ ID No. 5) | 27.7 | 0.49 | 61,770 |
| sAAPLpNA (SEQ ID No. 6) | 24.8 | 0.92 | 27,030 |
| sAAPHpNA (SEQ ID No. 7) | 24.0 | 1.09 | 21,960 |
| sAAPCpNA (SEQ ID No. 8) | 61.3 | 4.26 | 14,380 |
| sAAPNpNA (SEQ ID No. 9) | 35.3 | 2.91 | 12,160 |
| sAAPApNA (SEQ ID No. 10) | 36.1 | 5.29 | 6,826 |
| sAAPRpNA (SEQ ID No. 11) | 16.7 | 4.17 | 4,001 |
| sAAPKpNA (SEQ ID No. 12) | 10.9 | 4.22 | 2,577 |
| sAAPQpNA (SEQ ID No. 13) | 36.3 | 14.3 | 2,547 |
| sAAPSpNA (SEQ ID No. 14) | 7.05 | 3.73 | 1,893 |
| sAAPTpNA (SEQ ID No. 15) | 7.69 | 4.34 | 1,769 |
| sAAPVpNA (SEQ ID No. 16) | 0.53 | 1.08 | 1,422 |
| sAAPDpNA (SEQ ID No. 17) | 6.89 | 19.6 | 351 |

The different substrates were ranked by their ratio of $k_{cat}/K_M$ (also known as the catalytic efficiency). In addition to the substrates listed above, sAAPEpNA (SEQ ID NO. 18), sAAPGpNA (SEQ ID NO. 19) and sAAPIpNA (SEQ ID NO 20) were assayed, but the rates seen with them were too samll to be reliable. The substrates sAAPWpNA (SEQ ID NO. 21) and sAAPPpNA (SEQ ID NO. 22) were not assayed.

The results indicate that the enzyme has broad specificity preferring large nonpolar and polar amino acids over small nonpolar, small polar, or charged amino acids in the P1 position. There seems to be little preference for aromatic over aliphatic residues. Of the charged residues, the enzyme accommodates the basic amino acids, Arg and Lys, more than the acidic amino acids, Asp and Glu, indicating that either the larger size of the basic amino acids is preferred or that a positive charge is more easily accommodated than a negative charge in the P1 position. The presence of branching in the amino acid side chain seems to be tolerated when it occurs away from the peptide backbone (Leu) but much less when it occurs near the peptide backbone (Ile, Val).

Stability of SGPC to Urea and Guanidine

The effects of urea and guanidine on the stability of SGPC were measured by incubating the enzyme with different concentrations of the chaotropes then assaying the remaining activity. The urea and guanidine solutions were prepared in 20 mM $NH_4OAc$, pH 5.0. The SGPC at a final concentration of 100 ug/ml was incubated at 24° C. and pH 5.0, in the solutions listed below. The activity was assayed by first diluting an aliquot four-fold then placing a 5 ul aliquot of each diluted solution in a microtiter well, initiating the reaction by adding 95 ul of reaction mixture (50 ul of sodium bicine, pH 8.0, 35 ul of water and 10 ul of 20 mM sAAPFpNA (SEQ ID NO. 3) in DMSO). Measurements were done at 24° C. in triplicate using a microtiter plate reader. Results are reported as % activity compared to the non-treated control (20 mM $NH_4OAc$, pH 5.0).

| Solution | 1 hour | 24 hours |
|---|---|---|
| 20 mM $NH_4OAc$ | 100.0% | 100.0% |
| 2 M Urea | 103.5% | 98.1% |
| 4 M Urea | 118.2% | 112.4% |
| 6 M Urea | 116.4% | 112.9% |
| 2 M Guanidine | 125.7% | 105.7% |
| 4 M Guanidine | 130.4% | 55.8% |
| 6 M Guanidine | 98.0% | 10.1% |

Overall, the enzyme has unusual stability in the presence of urea and guanidine. Where 6 M urea or 6 M guanidine is usually sufficient to instantly denature most proteins, losses in activity are seen only at longer time periods at 24° C. The apparent increase in activity seen in the presence of urea and guanidine could be attributed to the stimulatory effects of small concentrations of these chaotropes in the assay (the concentrations of urea and guanididne in the assays were between 35 and 75 mM), an effect seen with other proteases.

The results indicate that 2 M to 6 M urea had very little effect on the activity of SGPC, since the activities at 24 hr were only slightly less than those at 1 hr. Guanidine at 2 M had a slight effect on the activity at 24 hr, but higher concentrations 4 M to 6 M began to show substantial losses of activity at 24 hr.

pH profile of SGPC

Figure 2:
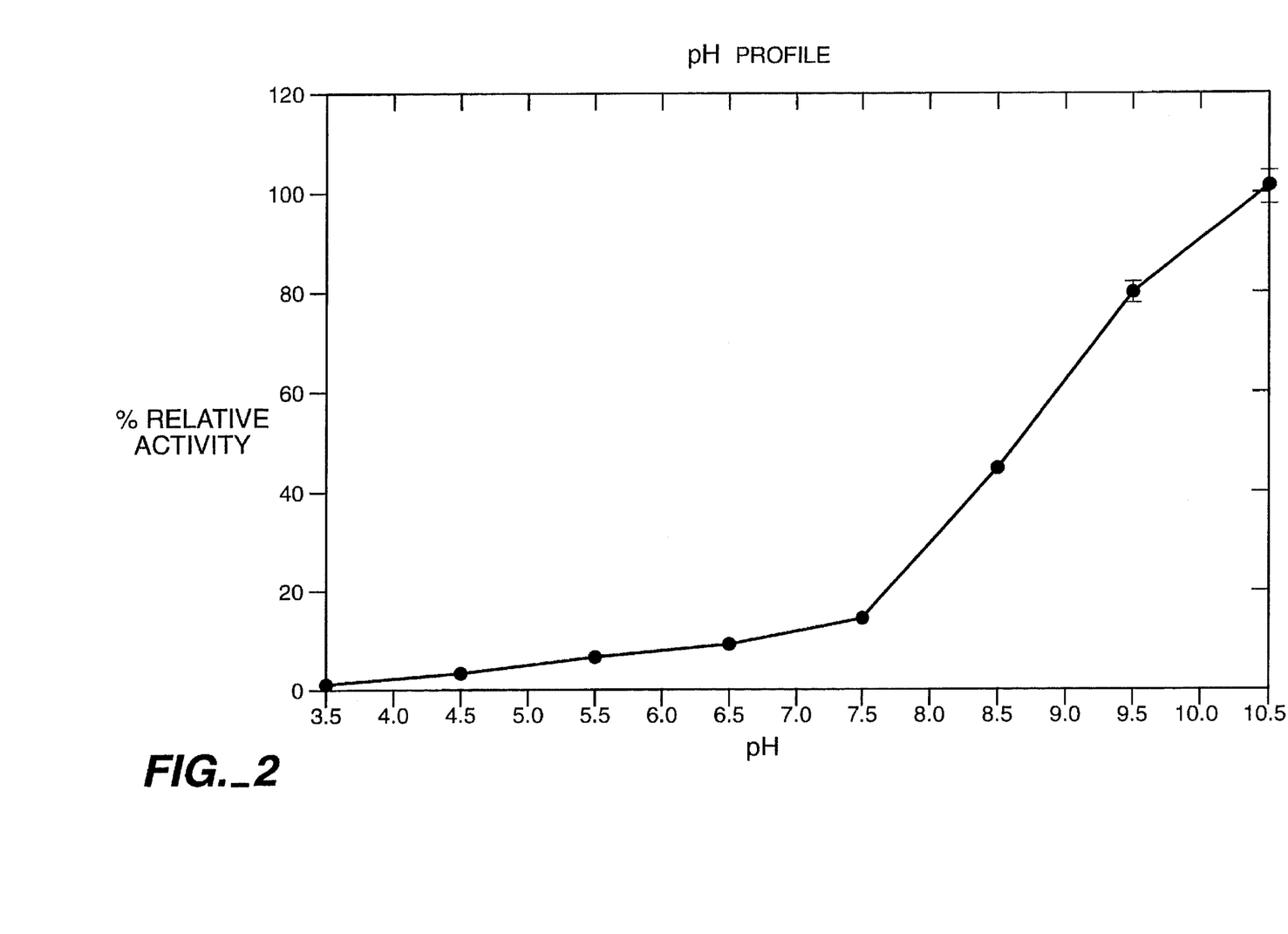
FIG. 2 is a graph of the pH profile of SGPC.

The pH profile was measured by assaying the enzyme at different pH values. A 5 ul aliquot of a 40 ug/ml solution of the enzyme in 2 mM $NH_4OAc$, pH 5.0, was placed in a well of a microtiter dish along with 50 ul of a 100 mM buffer stock. The reaction was initiated by adding 45 ul of SAAPF-pNA (SEQ ID NO. 3) in DMSO and water to give a final substrate concentration of 2 mM and a final DMSO concentration of 10%. Initial rates were measured in triplicate and the rates were plotted relative to the highest average rate. The graph is shown in FIG. 2. As can be seen, the enzyme has a highly alkaline pH optimum with the activity at pH 10.5 being 3 to 4 times that at pH 8.0. Higher pH values could not be tried with this substrate.

Modifications of the above described modes for carrying out the invention that are obvious to those of skill in the art of protein chemistry, molecular biology and detergent manufacture and related fields are intended to be within the scope of the following claims.

I claim:

1. A serine protease in substantially pure form derived from *Streptomyces griseus* var. *alkaliphilus* No. 33, said serine protease having enhanced stability against urea or guanidine and having an apparent molecular weight of about 19,000 daltons as determined by reducing SDS-polyacrylamide gel electrophoresis analysis.

2. The serine protease of claim 1, said serine protease comprising the N-terminal amino acid sequence:

| Tyr | Asp | Leu | Val | Gly | Gly | Asp | Ala | Tyr | Tyr | Ile | Gly |
|-----|-----|-----|-----|-----|-----|-----|-----|-----|-----|-----|-----|
| Asn | Gly | Arg | Cys | Ser | Ile | Gly | Phe | Ser | Val | Arg | Gln |
| Gly | Ser | Thr | Pro | Gly | Phe | Val | Thr | Ala | Gly | His | Cys |
| Gly | Ser | Val | Gly | Asn | Ala | Thr | Thr | Gly | Phe | Asn | Arg |
| Val | Ser | Gln | Gly | Thr | Phe | Arg | Gly | Ser | Trp | Phe | Pro |
| Gly | Arg | Asp | Met | Ala | Trp | Val | Ala | Val | Asn | Ser | Asn |
| Trp | Thr | Pro | Thr | Ser | Leu | Val | Arg | Asp | | | |
| (SEQ ID No: 1). | | | | | | | | | | | |

3. The serine protease of claim 2, further characterized as having the C-terminal amino acid sequence:

| Val | Thr | Gly | Ser | Thr | Gln | Ala | Thr | Val | Gly | Ser | Ser |
|---|---|---|---|---|---|---|---|---|---|---|---|
| Ile | Cys | Arg | Ser | Gly | Ser | Thr | Thr | Gly | Trp | Arg | Cys |
| Gly | Thr | Ile | Gln | Gln | His | Asn | Thr | Ser | Val | Thr | Tyr |
| Pro | Gln | Gly | Thr | Ile | Thr | Gly | Val | Thr | Arg | Thr | Ser |
| Ala | Cys | Ala | Gln | Pro | Gly | Asp | Ser | Gly | Gly | Ser | Phe |
| Ile | Ser | Gly | Thr | Gln | Ala | Gln | Gly | Val | Thr | Ser | Gly |
| Gly | Ser | Gly | Asn | Cys | Ser | Ile | Gly | Gly | Thr | Thr | Phe |
| His | Gln | Pro | Val | Asn | Pro | Ile | Leu | Ser | Gln | Tyr | Gly |
| Leu | Thr | Leu | Val | Arg | Ser | | | | | | |

(SEQ ID No: 2).

4. The setinc protease of claim 2, which has specificity for succinyl-Ala-Ala-Pro-Phe-para-nitroanilide (SEQ ID No: 3).

5. The serine protease of claim 2, which is inhibited by phenylmethylsulfonyl fluoride.

6. A cleaning composition comprising at least one surfactant and, in an amount effective to enhance removal of protein-containing materials, a setinc protease derived from *Streptomyces griseus* var. *alkaliphilus* No. 33, said serine protease having enhanced stability against urea or guanidine and having an apparent molecular weight of about 19,000 daltons as determined by reducing SDS-polyacrylamide gel electrophoresis analysis.

7. The cleaning composition of claim 6, which is a laundry detergent or additive composition.

8. The cleaning composition of claim 7, which is a liquid or granular formulation.

9. The cleaning composition of claim 7 or 8 wherein the serine protease is further characterized as having the C-terminal amino acid sequence:

| Val | Thr | Gly | Ser | Thr | Gln | Ala | Thr | Val | Gly | Ser | Ser | Ile | Cys |
|---|---|---|---|---|---|---|---|---|---|---|---|---|---|
| Arg | Ser | Gly | Ser | Thr | Thr | Gly | Trp | Arg | Cys | Gly | Thr | Ile | Gln |
| Gln | His | Asn | Thr | Ser | Val | Thr | Tyr | Pro | Gln | Gly | Thr | Ile | Thr |
| Gly | Val | Thr | Arg | Thr | Ser | Ala | Cys | Ala | Gln | Pro | Gly | Asp | Ser |
| Gly | Gly | Ser | Phe | Ile | Ser | Gly | Thr | Gln | Ala | Gln | Gly | Val | Thr |
| Ser | Gly | Gly | Ser | Gly | Asn | Cys | Ser | Ile | Gly | Gly | Thr | Thr | Phe |
| His | Gln | Pro | Val | Asn | Pro | Ile | Leu | Ser | Gln | Tyr | Gly | Leu | Thr |
| Leu | Val | Arg | Ser | | | | | | | | | | |

(SEQ ID No: 2).

10. A method of cleaning comprising contacting a surface soiled with proteinaceous material with a cleaning effective amount of the cleaning composition of claim 6.

11. The method of cleaning of claim 10 wherein the serine protease is further characterized as having the C-terminal amino acid sequence:

| Val | Thr | Gly | Ser | Thr | Gln | Ala | Thr | Val | Gly | Ser | Ser | Ile | Cys |
|---|---|---|---|---|---|---|---|---|---|---|---|---|---|
| Arg | Ser | Gly | Ser | Thr | Thr | Gly | Trp | Arg | Cys | Gly | Thr | Ile | Gln |
| Gln | His | Asn | Thr | Ser | Val | Thr | Tyr | Pro | Gln | Gly | Thr | Ile | Thr |
| Gly | Val | Thr | Arg | Thr | Ser | Ala | Cys | Ala | Gln | Pro | Gly | Asp | Ser |
| Gly | Gly | Ser | Phe | Ile | Ser | Gly | Thr | Gln | Ala | Gln | Gly | Val | Thr |
| Ser | Gly | Gly | Ser | Gly | Asn | Cys | Ser | Ile | Gly | Gly | Thr | Thr | Phe |
| His | Gln | Pro | Val | Asn | Pro | Ile | Leu | Ser | Gln | Tyr | Gly | Leu | Thr |
| Leu | Val | Arg | Ser | | | | | | | | | | |

(SEQ ID No: 2).

\* \* \* \* \*

UNITED STATES PATENT AND TRADEMARK OFFICE
CERTIFICATE OF CORRECTION

PATENT NO. : 5,646,028
DATED : July 8, 1997
INVENTOR(S) : Scott D. Leigh

It is certified that error appears in the above-indentified patent and that said Letters Patent is hereby corrected as shown below:

On the Title Page, Section [54] replace:
"[54]   ALKALINE SERINE PROTEASE *STREPTOMYCES GRISEUS* VAR. *ALKALIPHUS* HAVING ENHANCED STABILITY AGAINST UREA OR GUANIDINE"

with:
--[54]   ALKALINE SERINE PROTEASE FROM *STREPTOMYCES GRISEUS* VAR. *ALKALIPHUS* HAVING ENHANCED STABILITY AGAINST UREA OR GUANIDINE--

In Column 23, line 48, Claim 1:
replace "polyaerylamide gel electrophoresis analysis." with:

--polyacrylamide gel electrophoresis analysis.--

In Column 25, line 13, Claim 4:
replace "The setinc protease of claim 2, which has specificity for" with:

--The serine protease of claim 2, which has specificity for--

UNITED STATES PATENT AND TRADEMARK OFFICE
CERTIFICATE OF CORRECTION

PATENT NO. : 5,646,028
DATED : July 8, 1997
INVENTOR(S) : Scott D. Leigh

It is certified that error appears in the above-indentified patent and that said Letters Patent is hereby corrected as shown below:

In Column 25, line 20, Claim 6:
  replace "protein-containing materials, a setinc protease derived from" with:

--protein-containing materials, a serine protease derived from--

Signed and Sealed this

Sixth Day of January, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 81 amino acids
        ( B ) TYPE: amino acid
        ( D ) TOPOLOGY: linear     ( i i ) MOLECULE TYPE: protein     ( v ) FRAGMENT TYPE: N-terminal     ( v i ) ORIGINAL SOURCE:
        ( A ) ORGANISM: Streptomyces griseus     ( x i ) SEQUENCE DESCRIPTION: SEQ ID NO:1:

```
Tyr  Asp  Leu  Val  Gly  Gly  Asp  Ala  Tyr  Tyr  Ile  Gly  Asn  Gly  Arg  Cys
 1              5                        10                       15
Ser  Ile  Gly  Phe  Ser  Val  Arg  Gln  Gly  Ser  Thr  Pro  Gly  Phe  Val  Thr
              20                       25                       30
Ala  Gly  His  Cys  Gly  Ser  Val  Gly  Asn  Ala  Thr  Thr  Gly  Phe  Asn  Arg
```

|     |     | 35  |     |     |     | 40  |     |     |     | 45  |     |     |     |
| --- | --- | --- | --- | --- | --- | --- | --- | --- | --- | --- | --- | --- | --- |

Val Ser Gln Gly Thr Phe Arg Gly Ser Trp Phe Pro Gly Arg Asp Met
    50                            55                      60

Ala Trp Val Ala Val Asn Ser Asn Trp Thr Pro Thr Ser Leu Val Arg
  65                          70                    75                        80

Asp ( 2 ) INFORMATION FOR SEQ ID NO:2:

( i ) SEQUENCE CHARACTERISTICS:
        ( A ) LENGTH: 102 amino acids
        ( B ) TYPE: amino acid
        ( D ) TOPOLOGY: linear     ( i i ) MOLECULE TYPE: protein     ( v ) FRAGMENT TYPE: C-terminal     ( v i ) ORIGINAL SOURCE:
        ( A ) ORGANISM: Streptomyces griseus     ( x i ) SEQUENCE DESCRIPTION: SEQ ID NO:2:

Val Thr Gly Ser Thr Gln Ala Thr Val Gly Ser Ser Ile Cys Arg Ser
  1                  5                       10                  15

Gly Ser Thr Thr Gly Trp Arg Cys Gly Thr Ile Gln Gln His Asn Thr
                20                  25                    30

Ser Val Thr Tyr Pro Gln Gly Thr Ile Thr Gly Val Thr Arg Thr Ser
            35                  40                    45

Ala Cys Ala Gln Pro Gly Asp Ser Gly Gly Ser Phe Ile Ser Gly Thr
     50                    55                    60

Gln Ala Gln Gly Val Thr Ser Gly Gly Ser Gly Asn Cys Ser Ile Gly
  65                  70                    75                  80

Gly Thr Thr Phe His Gln Pro Val Asn Pro Ile Leu Ser Gln Tyr Gly
                85                  90                    95

Leu Thr Leu Val Arg Ser
            100

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:3:

Ala Ala Pro Phe
  1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:4:

Ala Ala Pro Met
  1

( 2 ) INFORMATION FOR SEQ ID NO:5:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: unknown ( i i ) MOLECULE TYPE: peptide ( x i ) SEQUENCE DESCRIPTION: SEQ ID NO:5:

Ala  Ala  Pro  Tyr
   1

( 2 ) INFORMATION FOR SEQ ID NO:6:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: unknown ( i i ) MOLECULE TYPE: peptide ( x i ) SEQUENCE DESCRIPTION: SEQ ID NO:6:

Ala  Ala  Pro  Leu
   1

( 2 ) INFORMATION FOR SEQ ID NO:7:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: unknown ( i i ) MOLECULE TYPE: peptide ( x i ) SEQUENCE DESCRIPTION: SEQ ID NO:7:

Ala  Ala  Pro  His
   1

( 2 ) INFORMATION FOR SEQ ID NO:8:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: unknown ( i i ) MOLECULE TYPE: peptide ( x i ) SEQUENCE DESCRIPTION: SEQ ID NO:8:

Ala  Ala  Pro  Cys
   1

( 2 ) INFORMATION FOR SEQ ID NO:9:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: unknown ( i i ) MOLECULE TYPE: peptide ( x i ) SEQUENCE DESCRIPTION: SEQ ID NO:9:

Ala  Ala  Pro  Asn
   1

( 2 ) INFORMATION FOR SEQ ID NO:10:

( i ) SEQUENCE CHARACTERISTICS:
　　　　　　　　( A ) LENGTH: 4 amino acids
　　　　　　　　( B ) TYPE: amino acid
　　　　　　　　( C ) STRANDEDNESS:
　　　　　　　　( D ) TOPOLOGY: unknown ( i i ) MOLECULE TYPE: peptide ( x i ) SEQUENCE DESCRIPTION: SEQ ID NO:10:

Ala　Ala　Pro　Ala
　　　1

( 2 ) INFORMATION FOR SEQ ID NO:11:

( i ) SEQUENCE CHARACTERISTICS:
　　　　　　　　( A ) LENGTH: 4 amino acids
　　　　　　　　( B ) TYPE: amino acid
　　　　　　　　( C ) STRANDEDNESS:
　　　　　　　　( D ) TOPOLOGY: unknown ( i i ) MOLECULE TYPE: peptide ( x i ) SEQUENCE DESCRIPTION: SEQ ID NO:11:

Ala　Ala　Pro　Arg
　　　1

( 2 ) INFORMATION FOR SEQ ID NO:12:

( i ) SEQUENCE CHARACTERISTICS:
　　　　　　　　( A ) LENGTH: 4 amino acids
　　　　　　　　( B ) TYPE: amino acid
　　　　　　　　( C ) STRANDEDNESS:
　　　　　　　　( D ) TOPOLOGY: unknown ( i i ) MOLECULE TYPE: peptide ( x i ) SEQUENCE DESCRIPTION: SEQ ID NO:12:

Ala　Ala　Pro　Lys
　　　1

( 2 ) INFORMATION FOR SEQ ID NO:13:

( i ) SEQUENCE CHARACTERISTICS:
　　　　　　　　( A ) LENGTH: 4 amino acids
　　　　　　　　( B ) TYPE: amino acid
　　　　　　　　( C ) STRANDEDNESS:
　　　　　　　　( D ) TOPOLOGY: unknown ( i i ) MOLECULE TYPE: peptide ( x i ) SEQUENCE DESCRIPTION: SEQ ID NO:13:

Ala　Ala　Pro　Gln
　　　1

( 2 ) INFORMATION FOR SEQ ID NO:14:

( i ) SEQUENCE CHARACTERISTICS:
　　　　　　　　( A ) LENGTH: 4 amino acids
　　　　　　　　( B ) TYPE: amino acid
　　　　　　　　( C ) STRANDEDNESS:
　　　　　　　　( D ) TOPOLOGY: unknown ( i i ) MOLECULE TYPE: peptide ( x i ) SEQUENCE DESCRIPTION: SEQ ID NO:14:

Ala　Ala　Pro　Ser
　　　1

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:15:

Ala Ala Pro Thr
    1

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:16:

Ala Ala Pro Val
    1

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:17:

Ala Ala Pro Asp
    1

( 2 ) INFORMATION FOR SEQ ID NO:18:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:18:

Ala Ala Pro Glu
    1

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:19:

Ala Ala Pro Gly
    1

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:20:

Ala Ala Pro Ile
    1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:21:

Ala Ala Pro Trp
    1

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: unknown     ( i i ) MOLECULE TYPE: peptide     ( x i ) SEQUENCE DESCRIPTION: SEQ ID NO:22:

Ala Ala Pro Pro
    1